United States Patent [19]

Meijer

[11] Patent Number: 5,097,326
[45] Date of Patent: Mar. 17, 1992

[54] IMAGE-AUDIO TRANSFORMATION SYSTEM

[75] Inventor: Peter B. L. Meijer, Eindhoven, Netherlands

[73] Assignee: U.S. Philips Corporation, New York, N.Y.

[21] Appl. No.: 558,680

[22] Filed: Jul. 27, 1990

[30] Foreign Application Priority Data

Jul. 27, 1989 [EP] European Pat. Off. ......... 89201979.5

[51] Int. Cl.⁵ ............................................. H04N 7/00
[52] U.S. Cl. ...................................... 358/94; 358/93; 381/124
[58] Field of Search ............... 358/94, 93, 105, 107; 381/124, 61

[56] References Cited

U.S. PATENT DOCUMENTS

| | | | |
|---|---|---|---|
| 3,907,434 | 9/1975 | Coles | 358/94 |
| 4,000,565 | 1/1977 | Overby et al. | 358/94 |
| 4,322,744 | 3/1982 | Stanton | 358/94 |
| 4,378,569 | 5/1983 | Dallas, Jr. | 358/94 |
| 4,658,427 | 4/1987 | Aubin | 358/94 |

FOREIGN PATENT DOCUMENTS

2596940 10/1987 France .

Primary Examiner—James J. Groody
Assistant Examiner—Michael H. Lee
Attorney, Agent, or Firm—Jack D. Slobod

[57] ABSTRACT

In a device for converting visual images into representative sound information especially for visually handicapped persons an image processing unit is provided with a pipelined architecture with a high level of parallelisum. An image is scanned in sequential vertical scanlines and the acoustical representatives of the scanlines are produced in real time. Each scanline acoustical representation is formed by sinusoidal contributions from each pixel in the scanline, the frequency of the contribution being determined by the position of the pixel in the scanline and the amplitude of the contribution being determined by the brightness of the pixel.

9 Claims, 7 Drawing Sheets

IMAGE-AUDIO TRANSFORMATION SYSTEM

BACKGROUND OF THE INVENTION

1. Field of the Invention

The invention relates to a transformation system for converting visual images into acoustical representations.

2. Description of the Related Art

An article of L. Kay in IEE Proceedings, Vol. 131, No. 7, September 1984, pp 559-576, reviews several mobility aids for totally blind or severely visually handicapped persons. With some of these aids visual information is converted into acoustical representations, e.g. the laser cane, but the conveyed amount of visual information is very low. In fact, these systems are mainly electronic analogs or extensions of the ordinary (long) cane, as they are obstacle detectors for a single direction pointed at. Direct stimulation of the visual cortex has also been tried, but up to now only with poor success. The disadvantage of having to apply brain surgery is an obvious obstacle in the development of this approach. Another possibility is to display an image by a matrix of tactile stimulators, using vibrotactile or electrocutaneous stimulation. The poor resolution of present modest-sized matrices may be a major reason for a lack of success in mobility.

Another approach mentioned in the Kay article is to concert acoustical representations. With this approach, called sonar, the problem of ambiguity arises, because very different configurations of obstacles may conceivably yield almost the same acoustic patterns. Another problem is that the complexity of an acoustic refraction pattern is very hard to interpret and requires extensive training. Here too the spatial resolution is rather low due to a far from optimal exploitation of available bandwidth. The range of sight is rather restricted in general. The document WO 02/00395 (which corresponds to U.S. Pat. No. 4,378,569) discloses a system in which an image sensed by a video signal generator is converted into sound information through a number of circuit channels corresponding with the number of pixels in a line of the image. This results in bulky circuitry mismatches in which may cause inaccuracies in the sound information generated.

SUMMARY OF THE INVENTION

It is an object of the invention to provide a transformation system in which the restrictions of known devices are avoided to a large extent, inaccuracy is avoided and the amount of circuit elements is substantially reduced enabling faithful real-time transformation. To this end a transformation system, recited in the preamble, is in accordance with the invention characterized in that, the transformation system implements the transformation in a manner which reduces the number of hardware processing channels down from a number corresponding with the number of image pixels to be transformed to derive an acoustic signal section.

The invention is based on the following basic considerations.

True visual input seems the most attractive, because it is known to provide an adequate description of the environment without distance limitations. Therefore a camera should be used as a source of data to be converted.

An acoustic representation will be used, because the human hearing system probably has, after the human visual system, the greatest available bandwidth. The greater the bandwidth, the larger the amount of information that can be transmitted in any given time interval. Furthermore, the human hearing system is known to be capable of processing and interpreting very complicated information, e.g. speech in a noisy environment, considering the flexibility of the human brain.

The mapping of an image into sound should be extremely simple from the viewpoint of a blind person. It must be understood at least for simple pictures in the beginning by any normal human being without much training and effort. This reduces psychological barriers.

A scanline approach will be used to distribute an image in time. Thus a much higher resolution for a given bandwidth is obtained. The time needed to transfer a single image must remain modest to make sure the entire image is grasped by short-term human memory for further interpretation. The transfer time must also be as small as possible to refresh an image as often as possible in order to have an up-to-date representation of reality, such as for moving objects. An upper limit to the conversion time will therefore be on the order of a few seconds.

The image-to-sound conversion must occur in real-time to be useful.

The system should be portable, low-power and low-cost to be suitable for private use in battery-operated mobility applications.

In a preferred embodiment storage means are incorporated to store digitized images so that image blurring during the conversion is eliminated.

A preferred embodiment of the invention is provided with a low-weight (portable), low-power (battery-feeded) image sensing system preferably incorporating digital data processing such as a CCD camera.

In a further preferred embodiment an image processing unit is based on orthogonally scanning a grid of pixels each pixel having one of a row of discrete brightness values. Such a grid may be built up by, for example, $64 \times 64$ pixels with, for example, sixteen possible brightness levels for every pixel.

A further embodiment comprises pipelined digital data processing for converting digitized image information into acoustical representation. Preferably a high degree of parallel processing is used in order to improve converting speed using the available structural processing lines efficiently.

A transformation system according to the invention is preferably suited to read out an image scanline-wise, for example in 64 scanlines with 64 pixels on each scanline. Preferably a scanline position is represented in time sequence and a pixel position is represented in frequency or vice versa while the brightness of a pixel is represented in amplitude of an acoustical representation.

In a further embodiment binaural stimulation with left and right acoustic representations is used to support the feeling for direction of movement. Two image sensors positioned apart a distance corresponding with the eye separation or simulating this geometry can be used to incorporate viewing for a better relative distance perspective.

Furthermore, the frequency distribution in and/or the duration of an acoustic representation can be made user programmable and/or selectable.

BRIEF DESCRIPTION OF THE DRAWING

Some embodiments according to the invention will be described in more detail with reference to the drawing. In the drawing:

FIG. 9a is a detailed schematic of a differentiation element in FIG. 5a,

FIG. 9b is a timing diagram relating input and output to the schematic of FIG. 9a.

DETAILED DESCRIPTION OF THE PREFERRED EMBODIMENTS

Figure 1:
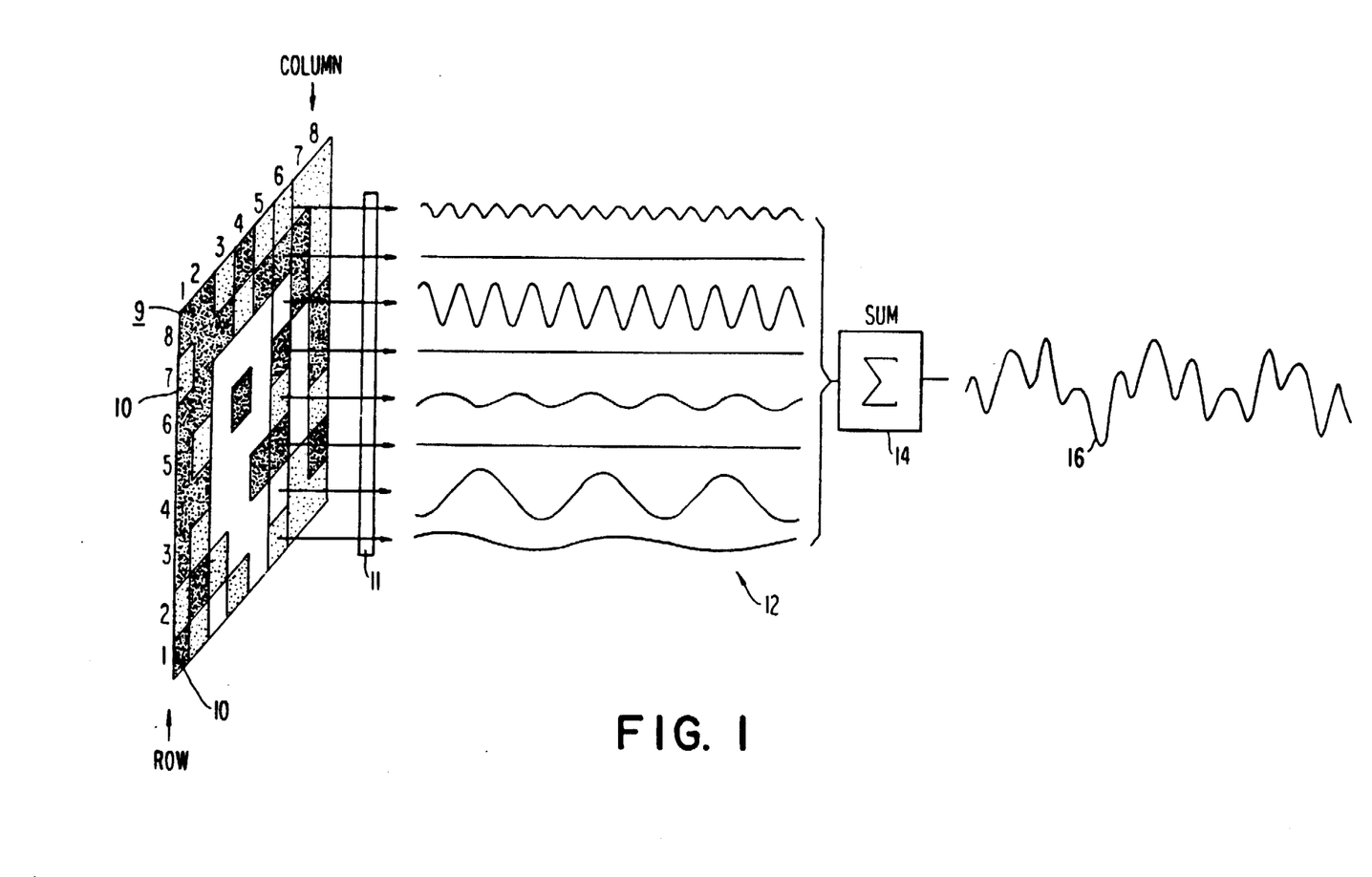
FIG. 1 is a pictorial illustrating basic principles of the transformations performed by the invention.

In order to put the description of the invention in perspective, it is useful to illustrate with a very simplified example, as given in FIG. 1, the principles of the way the invention transforms visual images into acoustical representations. The particular orientations and directions indicated in FIG. 1 and described below are not essential to the invention. For example, the transformation may be reconfigured for scanning from top to bottom instead of from left to right, without violating the principles of the invention. Other examples are the reversal of directions, such as scanning from right to left, or having high frequencies at low pixel positions etc. However, for the purpose of illustration particular choices for orientations and directions were made in the description, in accordance with FIG. 1, unless stated otherwise. Similarly, the particular number of rows, columns or brightness values in the image is not at all fundamental to the transformation. The example of FIG. 1 indicates for the sake of simplicity eight rows and eight columns with three brightness values, or greytones, per pixel. A more realistic example of a transformation system for visual images further described has 64 rows and 64 column, with sixteen brightness values per pixel.

FIG. 1 shows a chess-board-like visual image 9 partitioned into eight columns 1 through 8 and eight rows 1 through 8, giving 64 pixels 10. For simplicity the brightness of the image pixels can have one of three greytones: white, grey or black. This image can be considered to be scanned in successive vertical scanlines coinciding with any of the columns 1 through 8. An image processing unit 11 containing a digital representation of such an image, converts the vertical scanlines one after another into sound, in accordance with a particular scanning sequence, here from left to right. For any given vertical scanline, the position of a pixel in the column uniquely determines the frequency of an oscillator signal, while the brightness of this pixel uniquely determines the amplitude of this oscillator signal. The higher the position of a pixel in the column, the higher the frequency, and the brighter the pixel, the larger the amplitude. Signals 12 of all oscillator signals in the column of a particular scanline are summed and converted with the aid of a converting-summing unit 14 into acoustical signals 16. After this total signal has sounded for some time, the scanline moves to the next column, and the same conversion takes place. After all columns of the images have thus been converted into sound, a new and up-to-date image is stored, and the conversion starts anew. At this point in time the scanline jumps from the last, here rightmost column, to the first, here leftmost column of the image.

Due to the simplicity of this transformation, no training will be needed to interpret simple pictures. For example, one may consider a straight white line on a black background, running from the bottom left corner to the top right corner of the image. This will obviously result in a tone that starts having a low pitch and that increases steadily in pitch, until the high pitch of the top right pixel is reached. This sound is repeated over and over as a new frame (here with the same contents) is grabbed every few seconds. A white vertical line on a black background will sound as bandwidth-limited noise with a duration corresponding to the width of the line etc. After understanding the transformation of simple images into sound, one can imagine the sound of a picture before acutally hearing it. The interpretation of sound generated from transformation of more complicated pictures will require more training, as learning a new language does. But initially there is the bonus that understanding what sounds are generated from simple pictures may enhance the motivation of a user of the transformation system to proceed in practicing.

Figure 2:
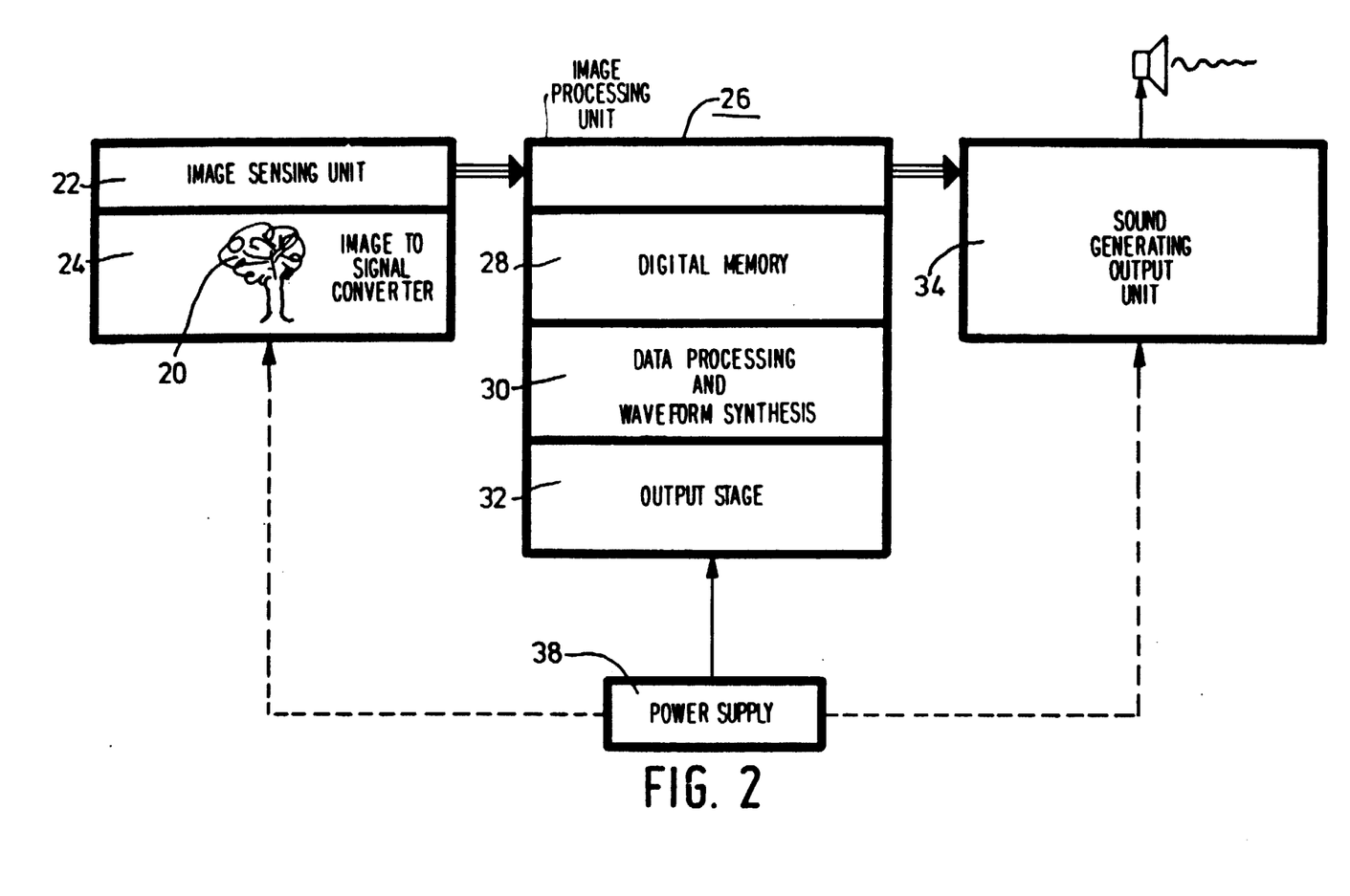
FIG. 2 is a block diagram of a system to perform transformations analogous to the transformations of FIG. 1.

An example of a system that performs image-to-sound conversion is depicted in FIG. 2. Images 20 are transformed into electronic signals by an image sensing unit 22 provided with a unit 24 for conversion of images into electronic signals, such as a camera. These electronic signals, which include synchronization signals, are processed by an image processing unit 26, in which a number of transformations take place. The image processing unit takes care of the conversion of analog electronic image signals into digital signals, which are stored in digital memory 28, after which digital data processing and waveform synthesis in a data processing and waveform synthesis unit 30 yields a digitized waveform, which is finally converted into analog electronic signals in a D/A conversion and analog output stage 32 for a sound generating output unit 34. The sound generating output unit could include headphones or any other system for converting electronic signals into sound, which does not exclude the possibility of using intermediate storage, such as a tape recorder. The image processing unit and, if they require a power supply, also the image sensing unit and/or the sound generation unit are powered by a power supply 38 as indicated in FIG. 2. Dashed lines indicate this condition, since for example headphones normally do not require an additional power supply. The power supply may be configured for battery operation.

In the following, architectural considerations for an image processing unit and in particular the digital data processing and waveform synthesis unit within the image processing unit, as indicated in FIG. 2, are described. Transformation of image into sound can be seen as a flow of data, undergoing a relatively complicated transformation. this complicated transformation can be decomposed into different processing stages, while reducing the complexity of the transformations taking place in individual stages. This will in general also allow for a reduction in processing time per stage. Data leaving a stage can be replaced by data leaving the previous stage. The processing of a number of data takes place in parallel, although in different stages of the total transformation. Thus a much larger data flow can be achieved by organizing the architecture as a pipeline, i.e. a sequence, of simple stages. In the design for the invention such a pipelined architecture has been applied. Without this kind of parallelism, a fast mainframe would have been needed to get the same real-time response. Obviously, the system would then not be portable, nor low-cost, nor low-power. The image processing unit can be seen as a special purpose computer with mainframe performance capabilities with respect to its restricted task, enabling real-time image-to-sound conversion using a clock frequency of only 2 MHz. This in turn enables the use of standard normal-speed components like EPROMs (Erasable Programmable Read-Only Memories) with 250 ns access times and static RAMs (static Random-Access Memories) with 150 ns access times, thereby reducing the cost of the system. Only the two phases of a single system clock are used for synchronization. The system emulates the behaviour of a superposition of 64 amplitude-controlled independent oscillators in the acoustic frequency range. There are reasons for selecting this number, although other numbers can be used without violating the principles of the invention. Yet, for simplicity of the description the number 64 and numbers derived from it are used on many occasions without further discussion. The 64 oscillators do not physically exist as 64 precisely tuned oscillator circuits, because this would probably give an unacceptably high system cost and size. Instead, the system employs the available digital speed to calculate in real-time what the superposition of 64 independent oscillators, having amplitudes controlled by the transformation would look like. To do this, it calculates a 16-bit sample of this superposition every 32 microseconds, thereby giving a 16-bit amplitude sample frequency of 31.25 kHz of the resulting acoustic signal (which, for comparison, is close to the 44.1 kHz 16 bit amplitude sample frequency of CD-players) The contributions to the superposition from all 64 oscillators must be determined in the 32 microseconds this allows for 500 nanoseconds per oscillator contribution. A sufficiently parallel system will therefore be able to do this job with a system clock frequency of 2 MHz.

Figure 3:
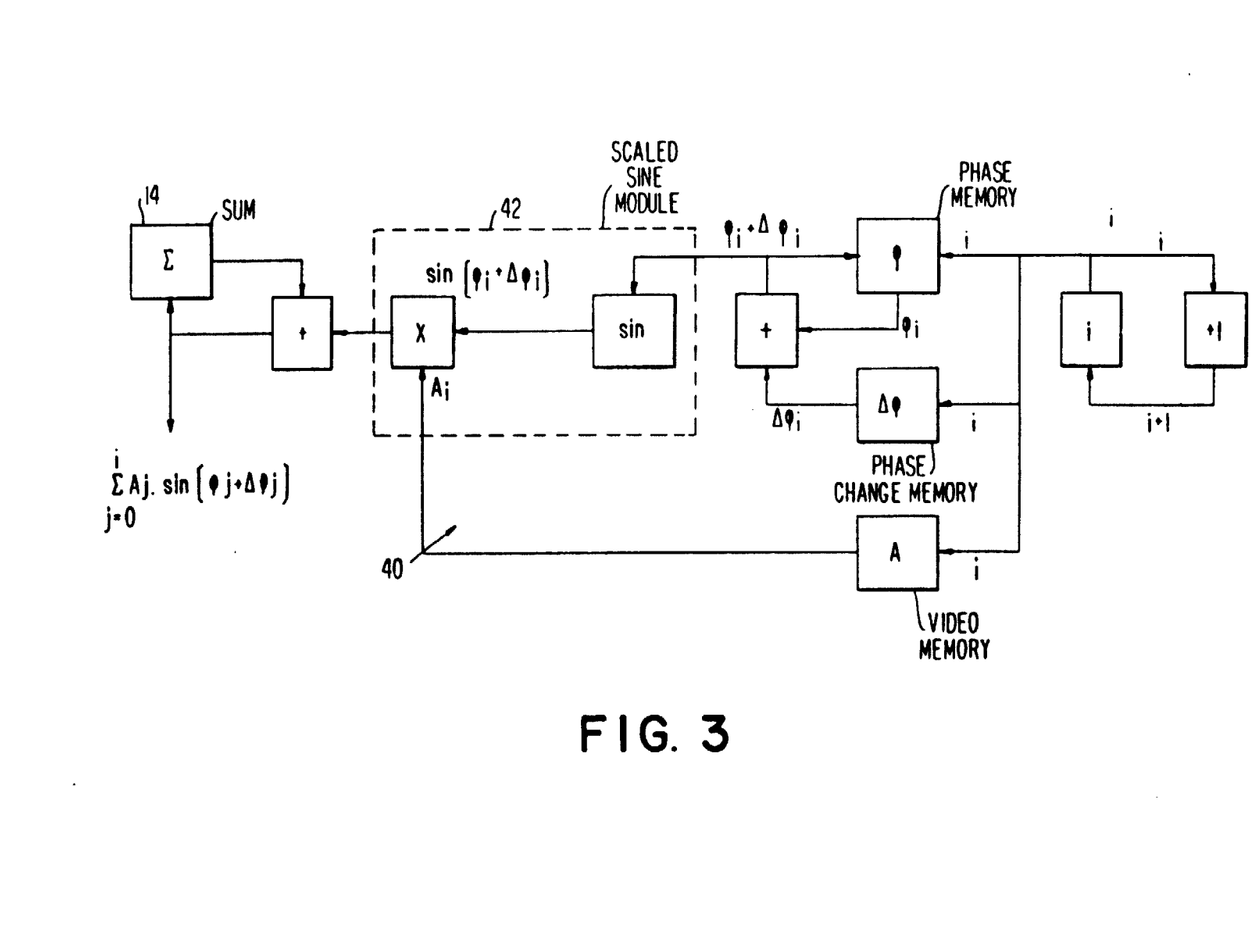
FIG. 3 is a block diagram illustrating the design and operation of a waveform synthesis stage within an image processing unit of FIG. 2.

FIG. 3 illustrates an algorithmic structure of the synthesis, by indicating schematically how a single waveform sample of the superposition waveform is calculated within the image processing unit 40. This single waveform sample corresponds directly with a single sound amplitude sample. The algorithmic structure of FIG. 3 can also be viewed as a block diagram of the waveform synthesis stage within the image processing unit of FIG. 2. For a particular scanline, as in the example of FIG. 1, all pixels i on that scanline are processed. For a pixel i, a new phase $\phi i + \Delta \phi i$ is calculated, by adding a phase increment from a phase change memory to a previous phase retrieved from accumulated phase memory memory. The result becomes the argument of a sine function in a scaled sine module 42, the resulting sine value being multiplied by a pixel brightness value Ai. In the image processing unit, this multiplication need not physically take place, but the results of one of all the possible multiplications may be retrieved from a memory module 42. The scaled sine value resulting from this (implicit) multiplication is added to results from previous pixels. When the results for all pixels i, 64 in the detailed design, have thus been accumulated, the overall result is a single sample of the emulated superposition of 64 oscillators.

In the waveform synthesis unit indicated schematically in FIG. 3, several pixels are processed simultaneously, although in different stages of the pipelines processing. A more detailed description of this parallelism is given in the following. In the system the following operations take place in parallel, once the image-to-sound conversion has started:

At clock phase L(ow), duration 250 ns, an address is calculated for phase-change memory containing the phase changes per time step of each of the 64 oscillators. This time step is the step corresponding to the final sample frequency of 1/64 times the system clock frequency (here 2 MHz), i.e. 32 us. The above address corresponds to the phase change of one particular oscillator. The new phase of another oscillator (calculated in earlier cycles) is stored, and at the same time used as an address for sine memory containing the sine as a function of phase, scaled by an amplitude measure. The 4-bit amplitude measure is simultaneously provided by video memory containing the frame as it was grabbed by a 4-bit analog-to-digital converter (ADC). The sum of scaled sine samples that came from previously handled oscillators is stored in a register. This is needed to obtain one final sample of the superposition of 64 amplitude-controlled digital oscillators.

At clock phase H(igh), duration 250 ns, an address is obtained for phase memory containing the present phases of all oscillators. The phase of an oscillator is read from this memory and added to its phase change, obtained from phase-change memory for which the address was calculated at clock phase L. A new address for the video memory is calculated. This address corresponds to the next pixel to be processed. A scaled sine value is read from sine memory. The scaled sine value of another oscillator is added to the sum of scaled sine values of previously handled oscillators. This is part of the process of calculating the superposition of 64 oscillators.

Figure 7:
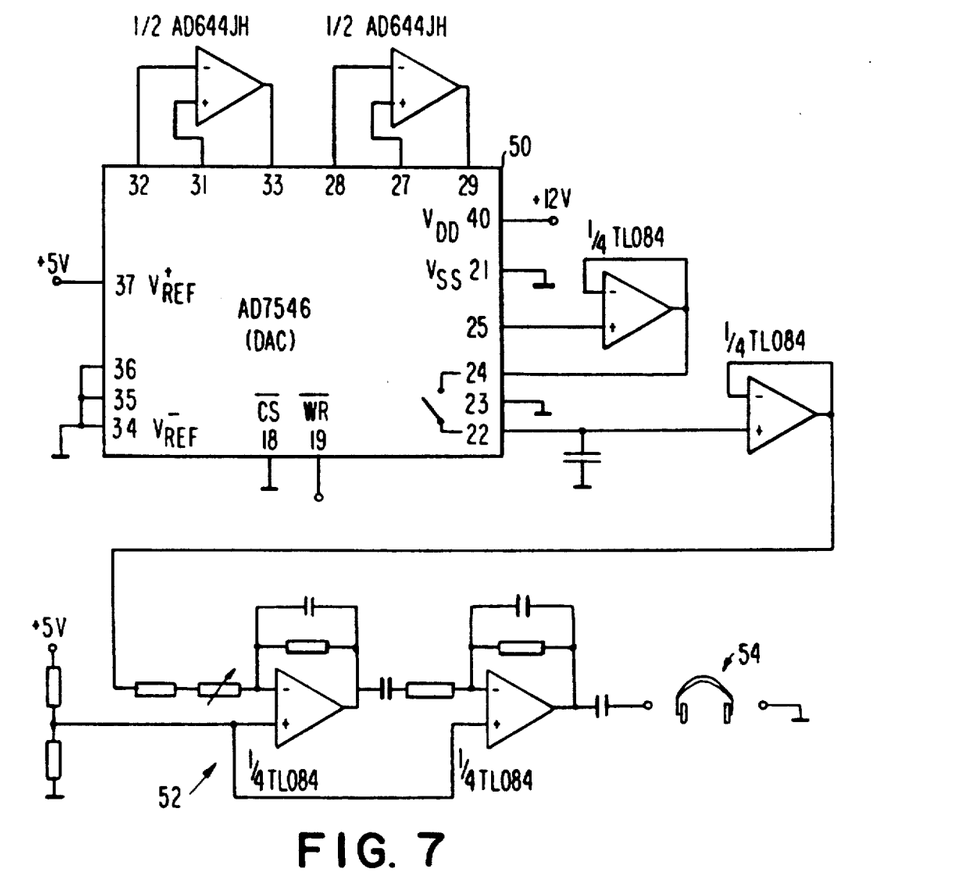

After 64 of such system clock cycles, i.e. 32 us, a sample of the superposition of the 64 amplitude-controlled oscillators is ready. This value can be sent to a 16-bit digital-to-analog converter DAC 50 and an analog output stage 52, and from there to a sound generating output unit such as a headphone 54 (FIG. 7).

In the above description, the clock phases H and L could have been interchanged, if this is done consistently throughout the text. The particular choice made is not fundamental, but a choice must be made.

As described above, both the sine amplitude scaling and the frequencies of the oscillators are determined by the contents of memory. The main reason for using memory instead of dedicated hardware is that this provides the ability to experiment with arbitrary mappings. An amplitude scaling other than multiplication by pixel brightness may give better contrast as perceived by the user. Non-equidistant oscillator frequencies will certainly give better frequency resolution as perceived by the user, because the human hearing system is more sensitive to differences in pitch at the lower end of the spectrum. In a preferred embodiment a "wohl-temperierte" set of frequencies is used, meaning that the next higher frequency is a constant factor times the previous frequency (i.e. they increase geometrically with pixel position). The resulting non-equidistant frequencies appear subjectively as almost equidistant tones. Another important reason for avoiding dedicated hardware is the cost. Memory is cheap, provided the transformation to be performed is simple enough to fit in a few memory chips. Additionally, a stereoscopic pair of images can be processed simultaneously in a similar manner to generate separate left and right acoustic representations suitable for application to headphones.

In a preferred embodiment a video camera is used as the input source. Whenever the previous image-to-sound conversion has finished, a video frame is grabbed and stored in electronic memory in the single frame time of the camera, e.g. one 50th of a second in most European video cameras, and one 60th of second in most American video cameras. This is to avoid blurred images due to moving objects or a moving camera. In the detailed design descriptions the use of the one 50th second frame time of the PAL television standard is assumed for the choice of time constants used to grab the video signal, but this is not fundamental to the invention. The image is stored as 64×64 pixels with one of 16 possible brightness values, i.e. grey-tones, for each pixel. Other numbers of pixels or brightness values could have been used, without violating the principles of the invention, but there are practical reasons for this particular choice. Then the next image-to-sound conversion starts. The electronic image can be considered as consisting of 64 vertical lines, each having 64 pixels. First the leftmost verical line is read from memory. Every pixel in this line is used to excite an associated digital harmonic oscillator. A pixel positioned higher in the vertical line corresponds to an oscillator of higher frequency (all in the acoustic range). The greater the brightness of a pixel, the larger the amplitude of its oscillator signal. Next all 64 oscillator signals are summed (superposed) to obtain a total signal with 64 Fourier components. This signal is sent to a DA-converter and output through headphones. After about 16 milliseconds the second (leftmost but one) vertical line is read from memory and treated the same way. This process continues until all 64 vertical lines have been converted into sound, which takes approximately one second. Then a new video frame is grabbed and the whole process repeats itself.

As stated before, the image is assumed to be scanned from the left to the right, without excluding other possibilities for scanning directions. The horizontal position of a pixel is then represented by the moment at which it excites its emulated oscillator. The vertical position of a pixel is represented by the pitch of its associated oscillator signal. The intensity, or brightness, of a pixel is represented by the intensity, or amplitude, of the sound corresponding to its associated oscillator signal.

The human hearing system is quite capable decomposing a complicated signal in its Fourier components (music, speech), which is precisely what is needed to interpret the vertical positions of pixels. The following sections will discuss the limits of Fourier decomposition in the bandwidth limited human hearing system, which will show that more than 64 independent oscillators would not be useful.

A picture is represented by the system as a time-varying vector of oscillator signals. The vector elements are the individual oscillator signals, each representing a pixel vertical position and brightness. The ear receives the entire vector as a superposition of oscillator signals. The human hearing system must be able to decompose the vector into its elements. The hearing system is known to be capable of performing Fourier decomposition to some extent. Therefore the oscillator signals will be made to correspond to Fourier components, i.e. scaled and shifted sines. The hearing system will then be able to reconstruct the frequencies of individual harmonic oscillators, and their approximate amplitude (i.e. reconstruct pixel heights and brightness).

Another related criterion for choosing a particular waveform is that the image-to-sound conversion should preferably be bijective to preserve information. A bijective mapping has an inverse, which means that no information is lost under such a mapping. To preserve a reversible one-to-one relation between pixels and oscillator signals, the oscillator signals corresponding to different pixels must obviously be distinguishable and separable, because the pixels are distinguishable and separable. The waveforms (functions) involved should therefore be orthogonal. A superposition of such functions will then give a uniquely determined vector in a countably infinite dimensional Hilbert space. A complete (but not normalized) orthogonal set of basis vectors in this Hilbert space is given by the functions 1, cos nt, sin nt, with n positive natural numbers. Of course only use a small finite subset of these functions will be used due to bandwidth limitations.

Other reasons for using harmonic oscillators are the following. Harmonic oscillation is the mechanical response of many physical systems after modest excitation. This stems from the fact that the driving force towards the equilibrium position of most solid objects is in first order approximation linearly dependent on the distance from the equilibrium position (Hooke's law). The resulting second order differential equation for position as a function of time has the sine as its solution (in the text amplitude and phase will implicitly be disregarded when not relevant, and just the term "sine" will be used for short), provided the damping can be neglected. The sine is therefore a basic function for natural sound, and it may expected that the human ear is well adapted to it. Furthermore, the construction of the human ear also suggests that this is the case, since the basal membrane has a difference in elasticity of a factor 100 when going from basis to apex. The transversal and longitudinal tension in the membrane is very small and will therefore not contribute to a further spectral decomposition. However, it should be noted that the brain may also contribute considerably to this analysis: with electro-physiological methods it has been found that the discharges in the hearing nerves follow the frequency of a pure sine sound up to 4 or 5 kHz. Because the firing rate of individual nerve cells is only about 300 Hz, there has to be a parallel system of nerves for processing these higher frequencies.

Periodic signals will give rise to a discrete spectrum in the frequency domain. In practice, periodic signals of infinite duration cannot be used, because the signal should reflect differences between successive scanlines and changes in the environment, thus breaking the periodicity. The Fourier transform of a single sine-piece of finite duration does not give a single spectral component, but a continuous spectrum with its maximum centred on its basic frequency. The requirement is that the spectrum of one sine-piece corresponding to a particular pixel is clearly distinguishable from the spectrum of a sine-piece corresponding to a neighbouring pixel in the vertical direction.

(In the following, I[. , .] denotes "the integral from . to ." while ω denotes the greek letter omega, ω0 denotes omega with subscript 0, PI denotes the greek letter PI etc. In general, a close typographical analog of the conventional mathematical symbols is used.

The Fourier transform is given by:

$$F(\omega) = I[-\inf. \inf]f(t) \exp(-j\omega t) dt$$

The Fourier transform of an arbitrary segment of a sine will now be calculated, by transforming the multiplication of a sine of infinite duration with a pulse of finite duration. This situation corresponds to a bright pixel at a particular height in a (vertical) scanline, surrounded by dark pixels at the same height in neighbouring scanlines.

The Fourier transform of a pulse with amplitude 1, starting at a and ending at b is calculated as:

$$f(\omega) = I[a,b]\exp(-j\omega t)dt = (2/\omega) \sin(\omega(b-a)/2) \exp(-j\omega(a+b)/2)$$

Next the modulation theorem is applied:

Fourier

Let  $f(t) \longleftrightarrow F(\omega)$. => $s(\tau) =$ $$f(t)\sin(\omega 0 t) \longleftrightarrow \frac{1}{2}j [F(\omega + \omega 0) - F(\omega - \omega 0))] = S(\omega)$$

Subsitution of the above expression for F(ω) and some rewriting finally gives, with $b-a = k*2PI/\omega 0$ for $|S(\omega)|$ 2.

A formula in which for $\omega >> 1$, $k >> 1$ and $|\omega 0 - \omega| << |\omega 0 + \omega|$, the highest peaks occur in the term:

$$G(\omega) = (kPI/\omega 0) \; 2 \; (\text{sinc}(k(\omega - \omega 0)PI/\omega 0)) \; 2$$

This simple formula for the term G(ω) will be used as an approximation of S(ω). It should be kept in mind that this approximation is only accurate near the maxima of S(ω), but that is sufficient for the purposes of this discussion.

The behaviour of |G(ω)|, scaled to its maximum, is given by the sinc function $|\text{sinc}(k(\omega - \omega 0)/\omega 0)|$ (with sinc(x)=sin (PI.x)/(PI.x). Apart from its main maximum 1 at x=0, the size of the maxima of |sinc(x)| can be approximated quite well by |1/(PI.x)|. The next largest maxima are found at x=-/+1.430 with size 0.217, i.e. a fifth of the main maximum. It seems reasonable to take as a rule of thumb, that a neighbouring frequency $\omega = \omega 0 + \Delta\omega 0$ should give an |x|-value no less than x1=1.430. At this limit the main maximum of the neighboring pixel spectrum with basic frequency ω0+Δω0 is located at the frequency of one of the next-to-main maxima of the original pixel spectrum with one of the next-to-main maxima of the original pixel spectrum with basic frequency ω0. So $k.\Delta\omega 0/\omega 0 >= x1$, when considering positive differences. Let the resolution to be obtained be N×N pixels. First the horizontal time separation between pixels is calculated. With a single image conversion time T seconds, there are T/N seconds per pixel: $T/N = b-a = k*2PI/\omega 0. =>$ with $\omega = 2PI.f$ this gives $k = f0.T/N$. The relation $k.\Delta f0/f0 >= x1$ should hold. Let the useful auditory bandwidth be give by B. An equidistant frequency distribution would then give Δf0=B/N (N pixels in a vertical line of the image). Combination of the above formula's yields (B.T)/(N 2)>=x1. Taking x1=1.430, an estimated bandwidth of 5 kHz and a conversion time of 1 second yields $N < = \text{SQRT}(B.T/x1) = 59$. Therefore the digital design is preferably made with N=64 (a power of 2 for easy design) to build a machine capable of achieving this theoretical maximum resolution estimate for a 1 second conversion time. A further embodiment preferably uses a non-equidistant set of frequencies to obtain a better compromise with the frequency sensitivity of the human hearing system. Whether that actually leads to a loss of resolution at the lower end of the spectrum (where Δf0 is smallest) is best tested esperimentally. This is because the human brain may well be capable of "filling in" details that may overcome a lack of local resolution, but that are suggested by the more global patterns. The brain can do a lot of image processing to extract useful information from noisy and blurred images. For example, vertices of a polygon can be suggested by incomplete edges. So care must be taken in the application of resolution estimates based only on local information and without a priori knowledge. These estimates may be too pessimistic.

IMAGE PROCESSING UNIT

Figure 4:
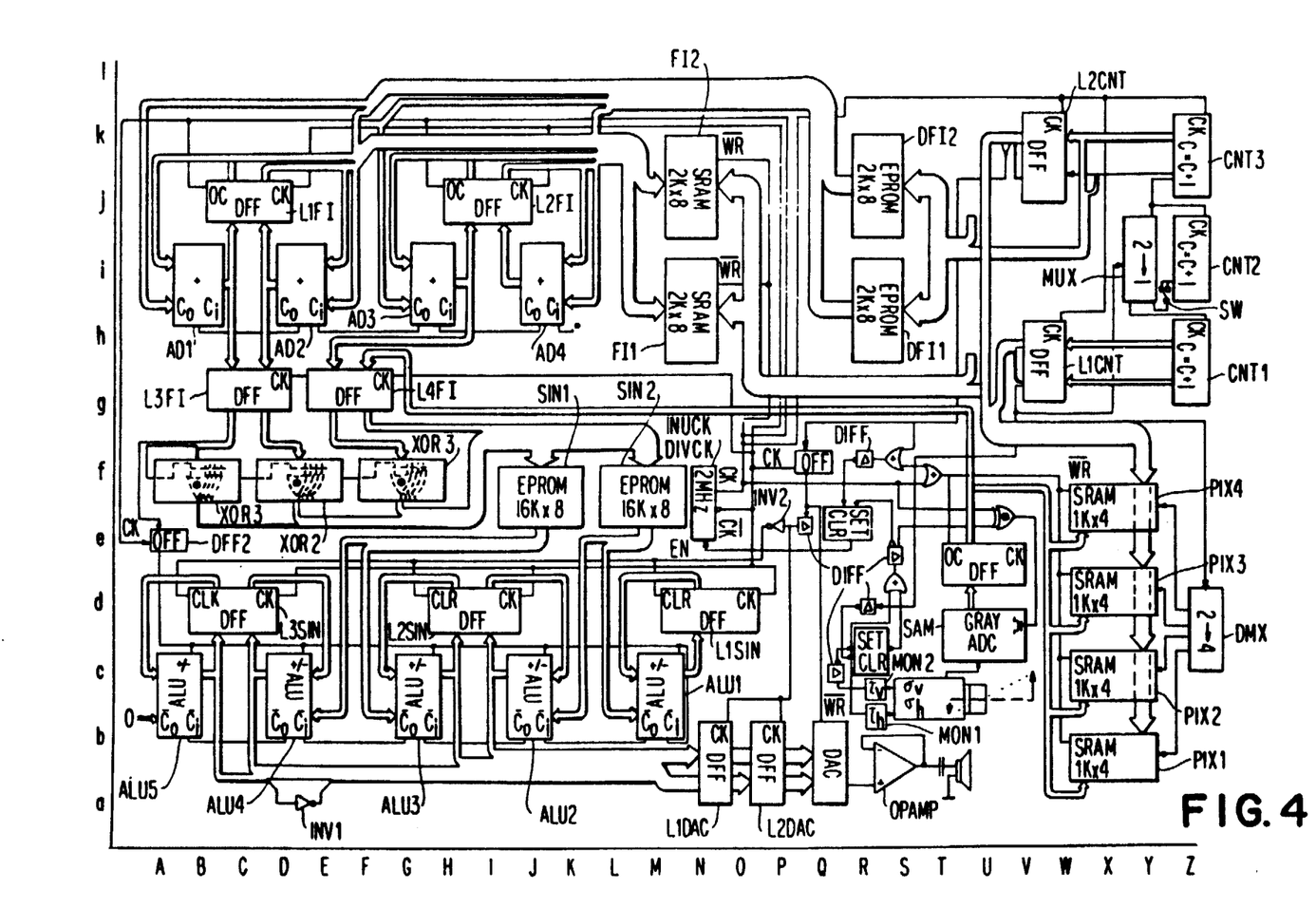
FIG. 4 is a flow chart showing the algorithmic structure of the image processing unit, of FIG. 2, FIG. 5 an illustration showing more detail of the control logic of the image processing unit of FIG. 4.

A rather detailed description of the design of an image processing unit and the resulting architecture is given in FIG. 4. The stream of data through the system will be followed to obtain a better insight in its operation. It is a pipelined system, such that major parts of the system are kept busy at all times. When a particular stage has completed an operation and shifted the result to the next stage, the next data item is shifted in from the previous stage for processing, and so on.

In FIG. 4 system buses are drawn having a width proportional to the number of bitlines. Because in the design there is not clearcut separation between the concepts of data buses and address buses no distinction is made in this respect: data generated by one part of the system are used as addresses by another part. Approximate coordinates in FIG. 4 are indicated by two-character Xy pairs. Apart from Xy coordinates also mnemonic names are given of the components as used in the description herein.

The 2 MHz system clock INVCK, DIVCK (at Ne) is preferably driven by an 8 MHz cristal. Starting at the upper right corner (at Zk) three dual 4-bit binary counters CNT1-3 are indicated that are driven by the system clock. These counters generate addresses for phase and phase change memories and also for video memory. The six lsb's, i.e. least significant bits, of these addresses always indicate a particular oscillator (phase and phase change memory) and its corresponding pixel position (video memory). During image-to-sound conversion, the counters are normally configured as one large 23-bit ripple-carry counter. During frame grabbing, the multiplexer MUX bypasses the 7-bit middle counter CNT2 to give a 128-fold increase in the frequencies of the most significant counter bits (the bottom counter). This is needed to grab a video frame within the 20 ms (50 Hz) television signal single frame time and thus avoid blurred images. The six msb's, i.e. most significant bits, of the bottom counter CNT1 always indicate a particular vertical scanline (horizontal position). The middle counter just ensures that it takes some time (and sound samples) before the next vertical scanline is going to be converted into sound. The 5 MHz input to the top counter CNT3 causes the output of the top counter to change every 500 ns. During image-to-sound conversion the output of the bottom counter changes every 16.4 ms, so the conversion of the whole image, i.e. 64 vertical scanlines, takes about 1.05 s. This can be most easily changed into a 2.1 second conversion time by using the full 8-bits of the middle counter, which is the purpose of the switch Sω at Yi. In that case the counters are configured as one large 24-bit counter. However, in the discussion a 7-bit middle counter is assumed (1.05 s conversion time), giving a 23-bit total counter (bit 0 through 22), unless stated otherwise. Addresses generated by the counters go unlatched to phase change EPROMs DFI1,2 (at Ri), while they are latched by L1CNT, L2CNT before going to phase SRAMs FI1,2 (at Ni). Thus care has been taken of the fact that the EPROMs are much slower (250 ns) than the SRAMs (150 ns). Therefore the EPROMs receive their addresses 250 ns earlier. A phase change of a particular oscillator read from the EPROMs is added to a present phase read from the SRAMs. Summation takes place in 4-bit full adders AD1-4 at (Bi-Ki), and the result is latched by octal latches L1FI, L2FI (at Cj, Ij) before being rewritten into the SRAMs. The new phase is also sent through latches L3FI, L4FI (at Dg), together with 4-bits pixel brightness information coming from video SRAMs PIX1-4 (at Xb-Xe). After a possible negation (ones complement) by exclusive-ORs XOR1-3 (at Bf-Gf), the phase and brightness are used as an address for the sine EPROMs SIN1,2 (at Kf). These give a sine value belonging to a phase range 0...PI/2 (1st quadrant), and scaled by the brightness value. The whole 2PI (four quadrant) phase range is covered by complementing the phase using exclusive-ORs and by bypassing the sine EPROMs with an extra sign bit through a line passing through a D-flipflop DFF2 at Ae; this flipflop gives a delay ensuring that the sign bit keeps pace with the rest of the sine bits. This sign bit determines whether the ALUs ALU1-5 (at Mc-Ac) add or subtract. The ALUs combine the results of all 64 emulated oscillators in one superposition sample. The latches L1SIN, L2SIN, L3SIN at Nd, Id, Cd are just for synchronization of the adding process. When the superposition has been obtained after 64 system clock cycles, the result is sent through latches L1DAC, L2DAC (at Oa) to a 16-bit digital-to-analog converter DAC (at (Qa). The inverter INVI at the bottom of FIG. 4 serves to give an offset to the summation process by the ALUs after clearing the latches at Cd, Id, Nd. The DAC (hexadecimal) input range is 0000H til FFFFH, so the starting value for the addition and subtraction process should be halfway at 8000OH to stay within this range after adding and subtracting 64 scaled sine samples. The design as indicated keeps the superposition almost always within this range without modulo effects (which would occur beyond 0000H and FFFFH), even for bright images. This is of importance, because overflows cause a distracting clocking or cracking noise. The average amplitude of the superposition will grow roughly with the square root of the number of independent oscillators times the average amplitudes of these oscillators. This can be seen from statistical considerations when applying the central limit theorem to the oscillator signals and treating them as stochastic variables, and simplifying to the worst case situation that all oscillators are at their amplitude value (+ or −). Therefore the average amplitude of such a 64 oscillator superposition will be about 8 times the amplitude of an individual oscillator, also assuming equal amplitudes of all oscillators as for a maximum brightness image. This factor 8 gives a 3-bit shift, which means that there must be provisions for handling at least 3 more bits. This is the purpose of ALU5 (at Ac), which provides 4 extra bits together with part of L3SIN (at Cd). The output of the DAC (at Qa) is sent through an analog output stage, indicated only symbolically by an operational amplifier OPAMP (at Sa). Finally the result reaches headphones (at Ta).

(*) Numerical calculations on sine superpositions showed that for a very bright image field, 3 bits would cause overflow during 16% of the time, whereas 4 bits would cause overflow during 0.5% of the time. Experimentally, this appears to be disturbing. Overflows for large and very bright image parts are heard as a disturbing "cracking" sound. Division of all sine values in the EPROMS by a factor of 4 cures this overflow problem with no noticable loss of sound quality (a 16-bit sine value would have been rather redundant anyway).

In the above a particular oscillator sample has more or less been followed through the system. When the image-to-sound conversion is complete, the frame grabbing process starts, triggered by bit 21 of counter CNT1-3.

Figures 5, 9A, 9B:
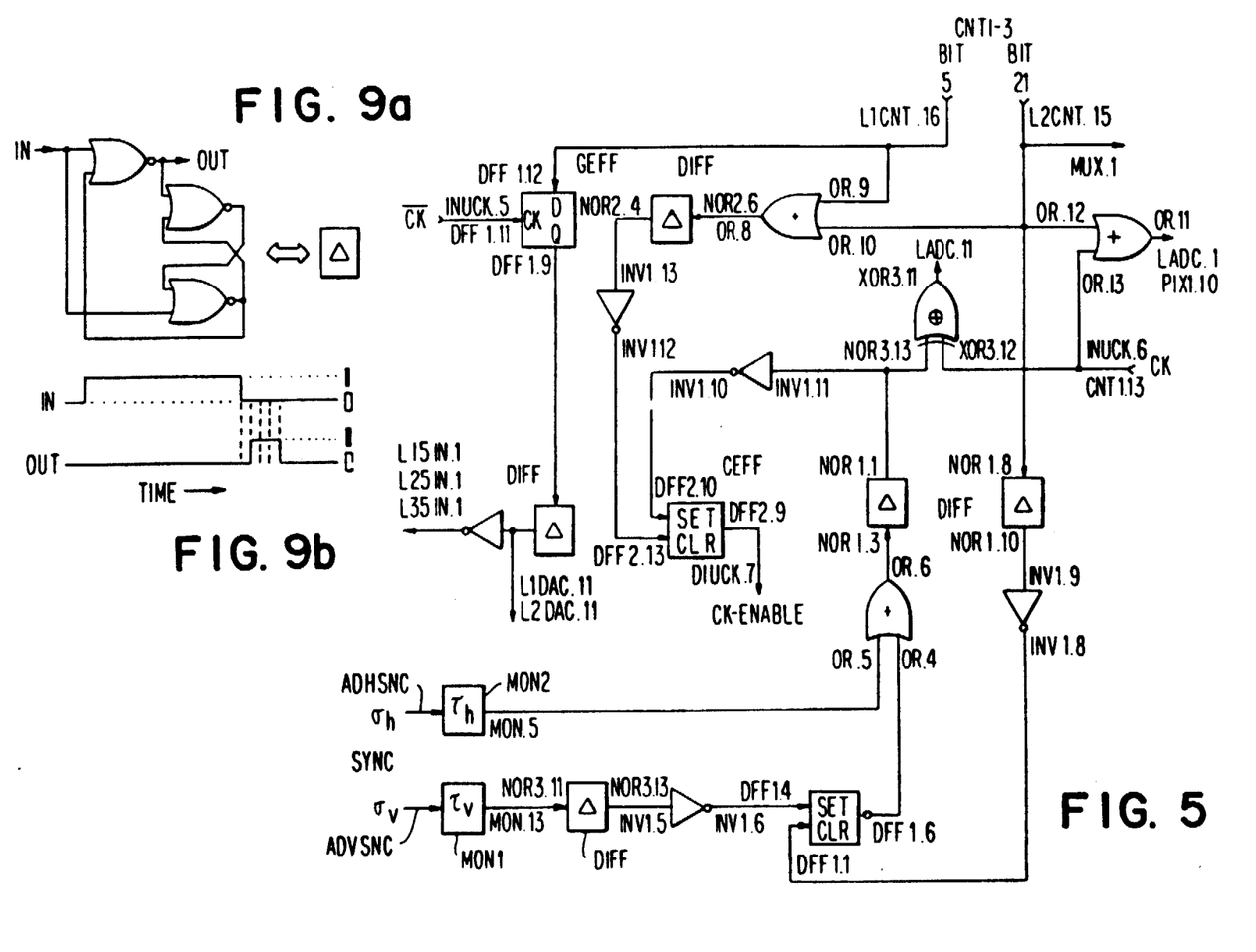
Figure 6:
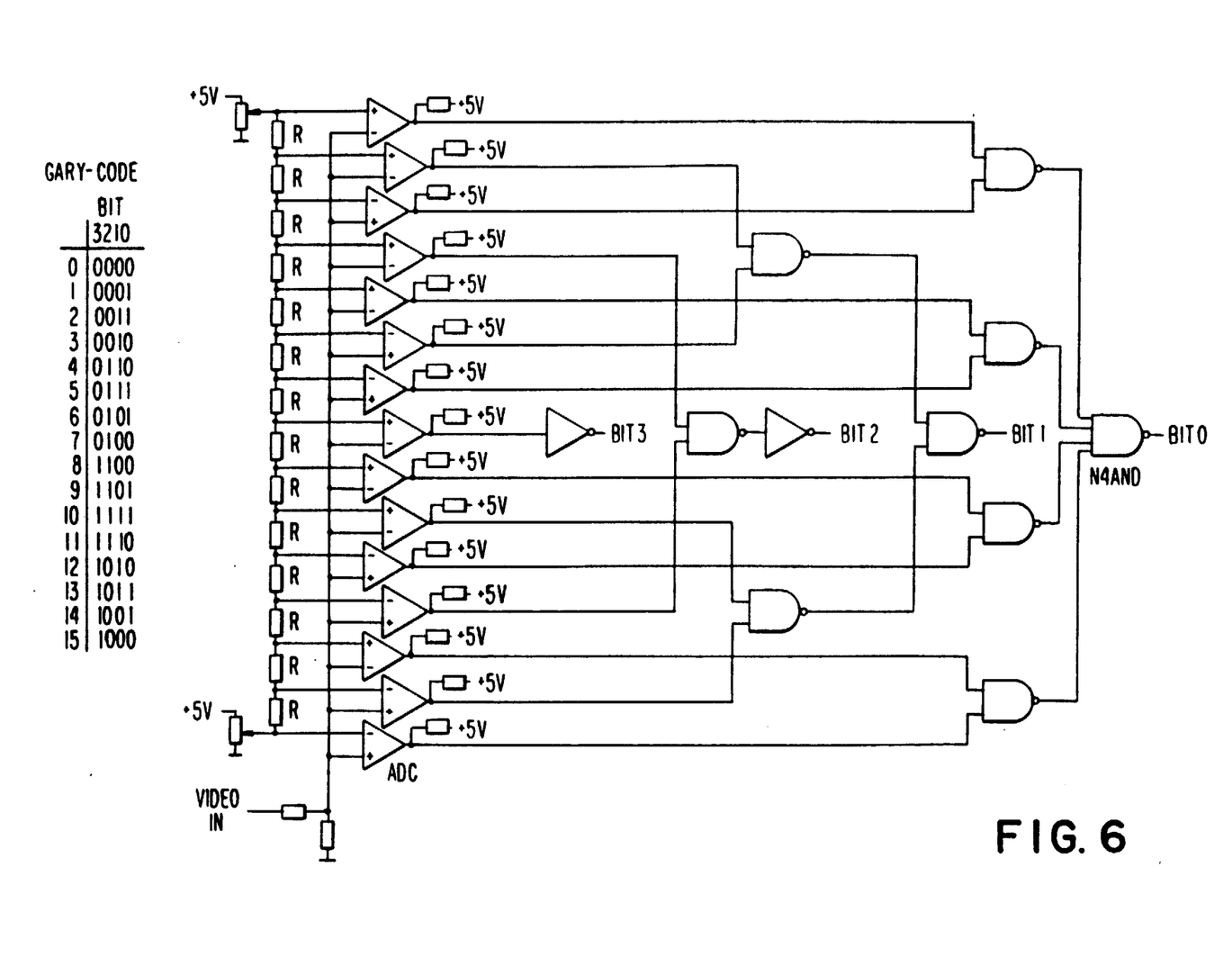
FIG. 6 is a block diagram of a Gray-code analog-to-digital converter for the image processing unit of FIG. 4, FIGS. 7 and 8 are block diagrams illustrating an analog output state for the image processing unit of FIG. 4.
Figure 8:
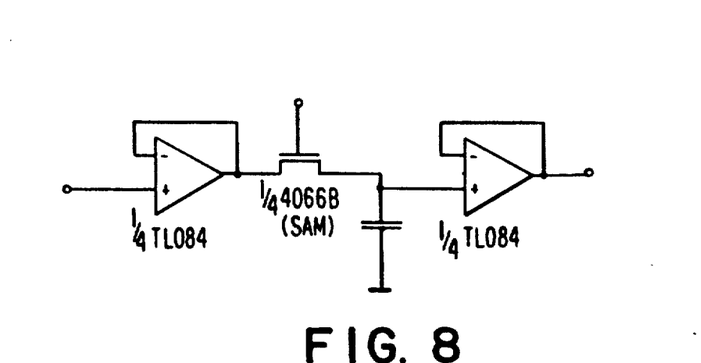

An analog video signal from an image sensing unit, such as a camera, indicated symbolically at Tb, is sent through a sample-and-hold circuit SAM, indicated in FIG. 4 as part of the ADC block at Uc, and converted to a 4-bit digital signal in Gray code by an A/D converter ADC1-15 (at Uc). A more detailed illustration of a sample and hold circuit is given in FIG. 8. This serves to reduce the probability of getting very inaccurate results due to transition states (spikes and glitches). In subsequent Gray-coded numbers only one bit at a time changes. The 4-bit code is then stored in video SRAM, i.e. PIX1-4 (at Xb-Xe), which receives its addresses from counters CNT1-3 (at Zg-Zk). Two bits of this address are used for chop selection by a demultiplexer DMX (at Zc). Components around Rd form the control Logic (or "random" logic) that takes care of detailed timing, synchronization and mode switching (frame grabbing versus image-to-sound conversion). This logic is depicted in more detail in FIG. 5. The meaning of the symbols in the control logic is the following. The tau's represent triggerable delays as monostable flip flops (monoflops) MON1 and MON2. Small signa's represent the horizontal and vertical synchronization pulses of the video signal ADHSNC and ADVSNC. The delta's represent differentiating subcircuits DIFF (illustrated in FIG. 9a) that generate a three-gate-delay spike output after the trailing edge of an input pulse as shown in FIG. 9b. This spike output is long enough to trigger subsequent circuitry.

In a prototype implementation according to the description in the invention, the whole image processing unit, i.e. the whole circuit for frame grabbing and image-to-sound conversion, has been implemented on a single circuit board measuring only 236×160 mm. This proves that the construction of a modest-sized portable system is possible. The only devices not on the board are the camera and the power supply. The camera that is used in the prototype system is the camera of the Philips 12T×3412 observation system. The power consumption of the system appeared to be quite low: a measured 4.4ω (5 V, 0.83A and 12 V, 21 mA) excluding the camera. This is obtained while using mainly LS TTL components. So the system is obviously practical for battery operation. The power consumption could be reduced even much further by applying CMOS ICs. LS TTL is attractive because of its combination of low cost and high electronic stability. The vidicon camera of the 12G×3412 has a specified power consumption of 2.7ω. This too could be much reduced by using a CCD camera instead, having a typical 100mω power consumption. Still, even the total power consumption of 7.1 ω could be supplied by a sufficient number of battery monocells (each 1.2 V, 4 A, hr) so as to last more than six hours, which should be more than enough for a full day.

To obtain 64 different oscillator frequencies, at the very least 64 different values are needed in the phase change memory, i.e. 6 bits. But to be able to vary the differences in frequency for successive oscillators, more flexibility is needed. For example, if those differences are to increase linearly with oscillator number, 63 different phase change differences have to be represented, rounded to 64 for convenience. Then 6 bits would be needed to indicate a basic oscillator phase change, and another 6 bits to represent the difference in phase change from the other oscillators phase changes. So 12 bits phase change accuracy is the minimum for a set of frequencies in which the differences between successive frequencies vary linearly with oscillator number. A good choice is the use of 16 bits accuracy in order to obtain extra freedom for non-linearly increasing frequency differences.

As illustrated in FIG. 4, not all 16 phase bits are used in calculating the sine values. The phase is truncated to its most significant 12 bits to free 4 bitlines that carry amplitude information from video memory to the sine memory for scaling. The truncation causes an error in the phases. The size of the error depends on the values of the four least significant phase bits. Because there is no intended special relation between a 31.25 kHz system sample frequency and an emulated oscillator signal, the four discarded bits will be considered as noise in successive samples of a particular oscillator. This is phase noise, resulting in frequency noise of the oscillator. The frequency noise must be much less than the frequency difference between neighbouring oscillators to prevent loss of resolution. The average frequency is still specified by the 16 bits phase accuracy, but the actual signal jumps a little around this frequency because of the truncation. This frequency noise can be calculated. Let the system clock have frequency F. Because the system clock supports 64 oscillators sequentially, F/64 oscillator samples per second are delivered. 12 Bits specify a sine value from the whole 2*PI radians period (10 bits specify PI/2 radians in the sine EPROMs). The phase error resulting from not using more bits (truncation) is therefore less than the least significant bit of the 12 bits, corresponding to a ¼ 12 period phase step error when going from one oscillator sample to the next. This in turn corresponds to a frequency noise of (F/64)/2 12=7.63 Hz for F=2 MHz. This is indeed much less then the frequency differences between neighbouring oscillators. For example, an equidistant frequency distribution of 64 oscillators over a bandwidth B gives steps in frequency of size B/(64-1). Let B=5 kHz, then this gives 79.4 Hz>>7.63 Hz. Many non-equidistant schemes also match the above condition for the frequency noise.

Because the phase calculations are 16 times more accurate (4 bits), it is noted, that a frequency in the phase change memory can be programmed with a resolution of about 0.5 Hz, which gives more than enough flexibility in choosing a non-equidistant frequency distribution.

VIDEO FRAME GRABBING

The mnemonic component names and two-character coordinates in the following text still refer to FIG. 4. A conventional video camera can be used on its side (rotated 90 degrees), such that image scanning may actually take place from bottom to top for each scanline, and from left to right for successive scanlines. This is just to have the same pixel order for frame grabbing as for image-to-sound conversion. Then just a single address generator suffices (the counter CNT1-3), which saves a lot of components. Thus system size and cost can be reduced. In order to avoid confusion, a frame grabbing system is described as if the camera were not tilted. This means that the conventional names for video signals are used. It should be kept in mind that with this convention a horizontal scanline of the video frame will represent a vertical scanline in the user image. The term "user" is used when indicating the image the user perceives.

A video frame is scanned by the camera 50 times per second, assuming the European PAL convention for convenience, as stated before, because other television standards would only slightly alter the descriptions. The scanning takes place from left to right (64 us per horizontal line, i.e. 15,625 Hz), and from top to bottom (312/313 lines). The 625-line PAL standard black and white video signal applies interleaving, alternatingly scanning 312 vertical lines in one 20 ms frame and 313 lines in the other. Because only a vertical resolution (horizontal to the user) of 64 pixels is needed, one arbitrary 20 ms frame is grabbed to minimize blurred images. The system frequency is independent of the camera frequency, so synchronization is needed for frame grabbing. The frame grabbing process is enabled when bit 21 of the counter CNT1-3 becomes low, which happens when the previous image-to-sound conversion is completed. The system then halts (clock disabled) until a vertical synchronization pulse in the video signal occurs (ADVSNC). Subsequently monoflop MON/adds another 1.52 ms delay. This ensures that the top margin of the frame is skipped (the left margin to the user, which is also invisible on the monitor). The other monoflop MON2 is then enabled, and triggered by a horizontal synchronization pulse in the video signal (ADHSNC). This adds another 15.2 us delay to skip the left margin of the frame (the bottom margin to the user, also invisible on the monitor). Then the system clock is enabled, allowing the counter to count freely while the first clock is enabled, allowing the counter to count freely while the first horizontal line (leftmost vertical user line) is scanned. During one clock phase the video signal is sampled in a sample-and-hold stage and converted into Gray-code by a set of comparators (not shown). During the other clock phase, when the 4-bit code has stabilized, the resulting digital brightness value (grey-tone) is latched and stored in video memory, while the sample-and-hold stage is opened for capturing the next video sample (pixel). The clock is disabled after 64 clock pulses, i.e. 32 us, which covers most of the area visible on the monitor. By then the first 64 pixels have been stored. After a horizontal synchronization pulse and a 15.2 us delay from the monoflop the clock is enabled again for the second line etc. Because of the counter configuration CNT1-3, with CNT2 bypassed, only every fourth line of the video signal causes an PIX1-4. So only the last of every four lines is actually remembered for later use. The others are overwritten. This is meant to make uniform use of the 312/313 line frame. Effectively grabbing only every fourth line ensures that the 64 vertical pixel resolution covers 64*4=256 lines of the frame, which is almost the whole visible field of the camera. After 256 scanlines, bit 21 of the counter becomes high, disabling the frame grabbing and restarting the image-to-sound conversion.

Frame grabbing is indicated by the following steps A through F:
A: bit 21 becomes low, disabling the system clock
B: a vertical synchronization pulse triggers the first monoflop
C: the delayed pulse from the first monoflop enables the second monoflop
D: a horizontal synchronization pulse triggers the second monoflop
E: the second monoflop enables the system clock
F: bit 5 of CNT1 disables the system clock after every 64 pulses

CONTROL LOGIC

Control logic or random logic having the function of controlling the cooperation and synchronization of different circuit blocks and pipeline stages is shown in more detail in FIG. 5. The labels A-F refer to the screen positions in the picture of the above schematic overview.

A] Bit 21 becomes low, thereby giving a low clear pulse at OFF.1 to grab-enable flipflop GEFF after differentation and inversion. This forces NOR1.3 to remain or become high, which causes NOR1.1 to stay low, as there is only one-sided differentiation. The constant high input at DFF2.10 is therefore inactive. When bit 21 gets low, so does biy 5, which causes a diffractiation pulse at NOR2.4. Through inversion this becomes a low clear pulse at DFF2.13 to the clock-enable flipflop GEFF. The output DFF2.9 will then become low and disable the system clock, DIVCK. Now only an external pulse can restart the system. The only external pulses come from the synchronization signals at MON.5 and MON.13. The horizontal sync pulse MON.5 cannot restart the system, because OR.5 is high. So the system has to wait until a vertical sync occurs at the time point indicated by label B, which after some delay sets at label C the grab-enable flipflop by pulling DFF1.4 low for a short time, so DFF1.6 becomes low. But then OR1.6 will have a high-to-low transition as soon as the delayed horizontal sync, position label D, at MON.5 becomes low, label E. MON.5 could already be low, which would cause a mutilated first scanline because of bad timing. However, the first three of every four scanlines are overwritten, so this does not matter.

E] OR.5 is constantly low and OR.4 just becomes low, thereby causing a high pulse at NOR1.1, which after inversion sets the clock-enable flipflop at DFF2.13. The system clock then starts running, and the counter CNT1-3 can generate addresses for memory. 64 pixels are stored in 64 system clock cycles, before counter bit 5 becomes low again (at label F, bit 21 stays low for a much longer time) and clears the clock-enable flipflop at DFF2.13 after differentiation (NOR2.4) and inversion (INV1.12). The image processing unit now waits (halts) until the next horizontal sync passes through MON.5, which enables the system clock again at label E in the way described above, OR.5 still being low. Then the next scanline with 64 pixels is stored in memory (PIX1-4), until bit 5 becomes low again at label F, which disables the system clock until the next delayed horizontal sync etc.

After 256 of these scans, effectively storing only every fourth line, i.e. 64 lines in all, bit 21 becomes high again, thereby forcing OR.8 to a constant high level, which prevents any further clock disable pulses at DFF2.13 as long as bit 21 stays high. A constant read signal is forced upon PIX1-4 for a high bit 21 through OR.11. This is the image-to-sound conversion phase, for which the synchronization is much less tricky than for the frame grabbing, during which two asynchronous subsystems, i.e. the image sensing unit and image processing unit, have to be synchronized. The major issues are now to prevent bus conflicts, shift data through the stages of the pipeline and output an audio sample every 64 system clock cycles. The latter task is handled at DFF1. 12. CNT1-3 count after the system clock signal goes low. It takes some time before bit 5 can go low because of the ripple carry counter, so it takes one extra clock cycle before DFF1.9 goes low. This delay prevents the loss of the last (64) oscillator contribution when the latches L1SIN-L2SIN are cleared and the last audio sample is shifted to the DA-converter through the latches L1DAC, L2DAC.

The exclusive-OR that controls the shift signals at LADC.11 prevents the "wrap-around" of the latest, rightmost, pixel samples of a horizontal scanline during frame grabbing. Without it, these samples would contribute to the leftmost pixel samples, because the latch of the AD-converter receives no shift pulses, nor does the sample-and-hold circuit, when the system clock is disabled (clock is low). The latch would therefore shift old information at its inputs when the system clock is enabled again and the clock goes high after a while, because the sample-and-hold gate opens only when the clock is high. The short extra pulse through NOR1.1 and XOR3.11 at the restart of the system clock flushes this old information and reloads the sample-and-hold circuit with information, i.e. a voltage, associated with the leftmost pixels. The time constant of the sample-and-hold circuit is approximately 10 ns, which is sufficiently short for reloading a reasonably accurate value for the first sample of a horizontal scanline, because the three-gate-delay pulse of the differentiator has a duration of approximately 30 ns. The AD-converter and Gray code encoder have sufficient time to digitize this newly sampled value before the system clock goes high after being enabled. So when the system clock becomes high, a proper first pixel value is shifted through the latch LADC into video memory PIX1-4.

In this section the timing of the image processing unit is considered in more detail. The discussion will therefore become more dependent on specific hardware choices. A closer look is needed at the image-to-sound conversion operations that take place in parallel during each phase of the s MHz system clock, giving 250 ns high (H) and low (L) levels. Time delay estimates are taken from manufacturer's data books and data sheets, mostly from Texas Instruments. Mnemonic names refer to the circuit design described heretofore. The process numbers 1 through 5 in front of the sets of operations taking place in parallel indicate the route taken by a particular oscillator sample. I.e. they indicate the stages in the pipeline. A sample starts at process 1, then proceeds to process 2 etc. Processes 1, 3 and 5 take place in parallel at clock=L, but they operate on different oscillator samples. The ame applies to processes 2 and 4 at clock=H.

| Clock → (250 ns) | |
|---|---|
| *Process 1: | Typical delay: |
| increment counters CNT1-3 | 70 ns |
| put count to address DFI EPROMs (not via latch) | 0 ns |
| use address to read DFI EPROMs | 250 ns |
| Total: | 320 ns |

The reading of DFI continues during process 2, so a total delay>250 ns is allowed for the process 1. DFT will need another 70 ns of the next clock phase H.

| *Process 3: | |
|---|---|
| shift sum to FI SRAMs, latches L1FI, L2FI (old address, count not yet shifted) | 20 ns |
| write sum into FI SRAMs (TI p. 8-14) | 150 ns |
| Total: | 170 ns |
| & (simultaneously): | |
| shift brighness from PIX to address SIN1,2 EPROMs, L3FI | max (20 ns |
| & shift phase to exclusive ORs XOR1-3, latches L3FI, L4FI | ,20 ns) |
| exclusive ORs give ones complement yes/no | 20 ns |
| use result as address to read SIN1,2 EPROMs | 250 ns |
| Total: | 290 ns |

The reading of SIN continues during process 4, so a total delay>250 ns is allowed for the second part of process 3. SIN will need another 40 ns of the next clock phase H.

| *process 5: | |
|---|---|
| shift superposition sample, latches L1SIN, L2SIN, L3SIN | 20 ns |
| Total: | 20 ns |
| & (only once every 64 clock cycles) | |
| clear superposition: clear latches L1SIN, L2SIN, L3SIN | |
| & shift superposition to DAC, latches L1DAC, L2DAC | |

The latter part of process 5 is triggered by a differentiating circuit to stay well within the 250 ns limit. The 64th cycle is detected by observing the delayed trailing edge of the 6th bit of counter CNT1.

| clock → H (250 ns) | |
|---|---|
| *process 2: | |
| shift count to address FI SRAMs, latches L1CNT, L2CNT | 20 ns |
| use address to read FI SRAMS | max(150 ns |
| & continue reading DFI EPROMs (process 1) | 70 ns |
| sum results FI and DFI in AD1-4 | 50 ns |
| Total: | 220 ns |
| & (simultaneously) | |
| shift count to address PIX1-4 SRAMs, latches L1CNT, L2CNT | 20 ns |
| use address to read PIX SRAMs | 150 ns |
| Total: | 170 ns |

Both totals are less than the 250 ns clock phase available.

| *process 4: | |
|---|---|
| continue reading SIN EPROMs (process 3) | 40 ns |
| add result to obtain superposition sample, ALU1-5 | 100 ns |

| *process 4: | |
|---|---|
| Total: | 140 ns |

In the schematic below the main actions taking place near the 64 clock cycles boundary are indicated schematically. Superposition is abbreviated to "sup". The numbers extending the words indicate the associated oscillator, i.e. 0 through 63.

| clock | counter | | |
|---|---|---|---|
| H250 ns | 60 | | |
| L250 ns | 61 | | |
| H | 61 | | |
| L | 62 | | |
| H | 62 | | |
| L | 63 | | Count63/Writephi62/Shiftsup61 |
| H | 63 | | Readphi63/Readsin62(tail)/addsup62 |
| L | 00 | | Count00/Writephi63/Shiftsup62 |
| H | 00 | | Readphi00/Readsin63(tail)/addsup63 |
| L | 01 | to DAC & clear sup: | Count01/Writephi00/Shiftsup63 |
| H | 01 | | Readphi01/Readsin00(tail)/addsup00 |
| L | 02 | | Count02/Writephi01/Shiftsup00 |
| H | 02 | | |
| L | 03 | | |
| H | 03 | | |

I claim:

1. Transformation system for converting a visual image signal representative of pixels in sequential scanlines through an image into an acoustic signal composed of sequential acoustic signal sections respectively corresponding to said scanlines, each acoustic signal section being formed of sequential output amplitude samples equally spaced apart by a predetermined time step and representing a superposition of signal contributions from respective pixels in the corresponding scanline, each signal contribution from a pixel being determined from a sinusoid frequency due to a position, of said pixel in the scanline and a sinusoid amplitude due to a brightness of said pixel, said system comprising:
  a processing unit having an image signal input for a current image and an output, said unit comprising:
  first memory means fed by said image signal input for storing sinusoid amplitudes respectively due to brightnesses of the pixels in a current scanline to be processed in the current image;
  second memory means for storing phase increments due to the pixel positions in the current scanline respectively corresponding to sinusoid frequencies due to the pixel positions in said current scanline times the predetermined time step;
  third memory means for storing cumulated phases for the signal contributions from the respective pixels positions in said current scanline to a currently processed output amplitude sample;
  first summing means responsive to data outputs of said first and second memory means for forming a current cumulated phase for the signal contribution from a currently processed pixel position in said current scanline as a sum of a last cumulated phase for the signal contribution from said currently processed pixel position, stored in said second memory means, and the phase increment due to said currently processed pixel position, stored in said first memory means, and for updating said third memory means with said sum;

sine means responsive to a data output of the first memory means and to the current cumulated phase formed by the summing means for forming a signal contribution to the currently processed output amplitude sample due to the currently processed pixel position as a product of the sinusoid amplitude and a sinusoidal function of said current cumulated phase for the currently processed pixel position; and second summing means responsive to the output of the sine means for forming a cumulative sum of contributions to the currently processed amplitude sample due to all pixel positions in the current scanline, having an output comprising the output of said image processing unit;

image input means coupled to said image signal input for successively updating the current image at a frame rate; and audio transducer means responsive to the output of said image processing unit for successively forming the acoustic signal sections corresponding to each successive current scanline.

2. The system as claimed in claim 1, wherein said sine means comprises a ROM containing scaled sine values at memory addresses given by the combination of the current cumulated phase and sinusoid amplitude for the currently processed pixel position.

3. Transformation system as claimed in claim 1, characterized in that said image input means comprises a portable image sensing system for feeding said image signal input of said image processing unit.

4. Transformation system as claimed in claim 1, wherein said image input means updates said current image at a television frame rate and said image processing unit operates in real-time on successively updated current images.

5. Transformation system as claimed in claim 4, characterized in that said image processing unit comprises a pipelined digital processing architecture.

6. Transformation system as claimed in claim 1, wherein each scanline is a pixel column.

7. Transformation method for converting a visual image signal representative of pixels of sequential scanlines through an image into an acoustic signal composed of sequential acoustic signal sections respectively corresponding to said scanlines, each acoustic signal section being formed of sequential output amplitude samples equally spaced apart by a predetermined time step and representing a superposition of signal contributions from respective pixels in the corresponding scanline, each signal contribution from a pixel being determined from a sinusoid frequency due to a position of said pixel in the scanline and a sinusoid amplitude due to a brightness of said pixel, said method comprising:

first storing sinusoid amplitudes due to brightnesses of pixels in a current scanline to be processed;

second storing phase increments due to the pixel positions in the current scanline respectively corresponding to the sinusoid frequencies due to the pixel positions in the scanline times the predetermined time step;

third storing cumulated phases for the signal contributions from the respective pixel positions in said current scanline to a currently processed output amplitude sample;

first forming a current cumulated phase for the signal contribution from a currently processed pixel position in said current scanline as a sum of the third stored cumulated phase for said currently processed pixel position and the second stored phase increment for due to the currently processed pixel position, and updating the third stored cumulative phase for the currently processed pixel position with said sum;

second forming the signal contribution to the currently processed output amplitude sample due to the currently processed pixel position as a product of the sinusoid amplitude and a sinusoidal function of said current cumulated phase for the currently processed pixel position; and third forming a cumulative sum of the second formed contributions to the currently processed amplitude sample due to all pixel positions in said scanline.

8. The method as claimed in claim 7, wherein said second forming comprises addressing a ROM containing scaled sine values at an address formed by the combination of the current cumulated phase and sinusoid amplitude for the currently processed pixel position.

9. A method as claimed in claim 7, wherein the sinusoid frequency associated with each pixel position increases geometrically with change of pixel position in a predetermined direction along a scan line.

* * * * *